United States Patent
Jang et al.

(10) Patent No.: US 8,423,295 B2
(45) Date of Patent: Apr. 16, 2013

(54) METHOD OF OUTPUTTING BODY INFORMATION AND APPARATUS THEREFOR

(75) Inventors: Woo-young Jang, Seoul (KR);
Myung-hwan Yun, Seoul (KR);
Dong-soo Suh, Yeongi-gun (KR);
Jin-wook Oh, Busan-si (KR); Kyung-ho Kim, Yongin-si (KR); Hong-sig Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 2071 days.

(21) Appl. No.: 11/445,152

(22) Filed: Jun. 2, 2006

(65) Prior Publication Data
US 2007/0038151 A1 Feb. 15, 2007

(30) Foreign Application Priority Data

Jun. 20, 2005 (KR) ........................ 10-2005-0053057

(51) Int. Cl.
*G01N 33/48* (2006.01)
*G01N 33/50* (2006.01)
*A61B 5/103* (2006.01)

(52) U.S. Cl.
USPC .............................. 702/19; 600/587; 382/100

(58) Field of Classification Search .................. None
See application file for complete search history.

(56) References Cited

U.S. PATENT DOCUMENTS 7,809,153 B2 * 10/2010 Bravomalo et al. ........... 382/100
2006/0002600 A1 * 1/2006 Martel-Pelletier et al. ... 382/128

FOREIGN PATENT DOCUMENTS

| JP | 2002-259474 | 9/2002 |
| KR | 10-2000-0030384 | 6/2000 |
| KR | 10-2000-0053954 | 9/2000 |
| KR | 10-2000-0054547 | 9/2000 |
| KR | 10-2001-0088702 | 9/2001 |
| KR | 10-2002-0050251 | 6/2002 |
| KR | 10-2003-0031945 | 4/2003 |

OTHER PUBLICATIONS

Booker et al. Computing in Science & Engineering, 1999 vol. 1 (4), pp. 26-35.*
Chi et al. IEEE Computer Graphics and Applications, 1998, pp. 30-38.*
Nelson B. Academic Emergency Medicine, vol. 5, Issue 7, 739-744, 1998.*

* cited by examiner

*Primary Examiner* — Michael Borin
(74) *Attorney, Agent, or Firm* — Staas & Halsey LLP

(57) ABSTRACT

A method and an apparatus for outputting body information of a user. The method of outputting the body information of a user comprises: designating coordinate points of the body information according to first, second, and third body information on a three-dimensional coordinate having the first, second, and third coordinates as coordinate axes; and outputting comparison information between the user body figure and the average body figure from the distance between the coordinate point of the body information of the average body figure designated on a three-dimensional coordinate in advance and the coordinate point of the body information of the user.

33 Claims, 9 Drawing Sheets

FIG. 2

SEX: MALE   AGE: 20 - 24   ITEM : THIGH CIRCUMFERENCE                                                                                                                                                                           (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 344 | 563.8 | 48.2 | 470 | 489 | 500 | 531 | 564 | 590 | 632 | 650 | 704 | 0.46 |

SEX: MALE   AGE: 25 - 29   ITEM : THIGH CIRCUMFERENCE                                                                                                                                                                           (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 336 | 566.2 | 43.2 | 475 | 495 | 510 | 538 | 564 | 592 | 621 | 639 | 675 | 0.42 |

SEX: MALE   AGE: 30 - 34   ITEM : THIGH CIRCUMFERENCE                                                                                                                                                                           (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 353 | 561.1 | 45.2 | 455 | 482 | 500 | 531 | 561 | 590 | 618 | 638 | 671 | 0.43 |

SEX: MALE   AGE: 35 - 39   ITEM : THIGH CIRCUMFERENCE                                                                                                                                                                           (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 350 | 566.5 | 40.8 | 478 | 502 | 519 | 542 | 562 | 592 | 615 | 638 | 670 | 0.38 |

SEX: MALE   AGE: 20 - 24   ITEM : STOMACH CIRCUMFERENCE                                                                                                                                                                         (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 344 | 796.8 | 77.8 | 669 | 695 | 712 | 746 | 784 | 835 | 890 | 940 | 1038 | 0.53 |

SEX: MALE   AGE: 25 - 29   ITEM : STOMACH CIRCUMFERENCE                                                                                                                                                                         (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 336 | 813.4 | 68 | 680 | 720 | 733 | 764 | 810 | 854 | 908 | 937 | 981 | 0.46 |

SEX: MALE   AGE: 30 - 34   ITEM : STOMACH CIRCUMFERENCE                                                                                                                                                                         (UNIT : mm)

| MEASUREMENT FREQUENCY | AVERAGE | STANDARD DEVIATION | 1st percentile | 5th percentile | 10th percentile | 25th percentile | 50th percentile | 75th percentile | 90th percentile | 95th percentile | 99th percentile | CV |
|---|---|---|---|---|---|---|---|---|---|---|---|---|
| 352 | 842.4 | 80.3 | 681 | 712 | 740 | 787 | 840 | 899 | 951 | 976 | 1042 | 0.51 |

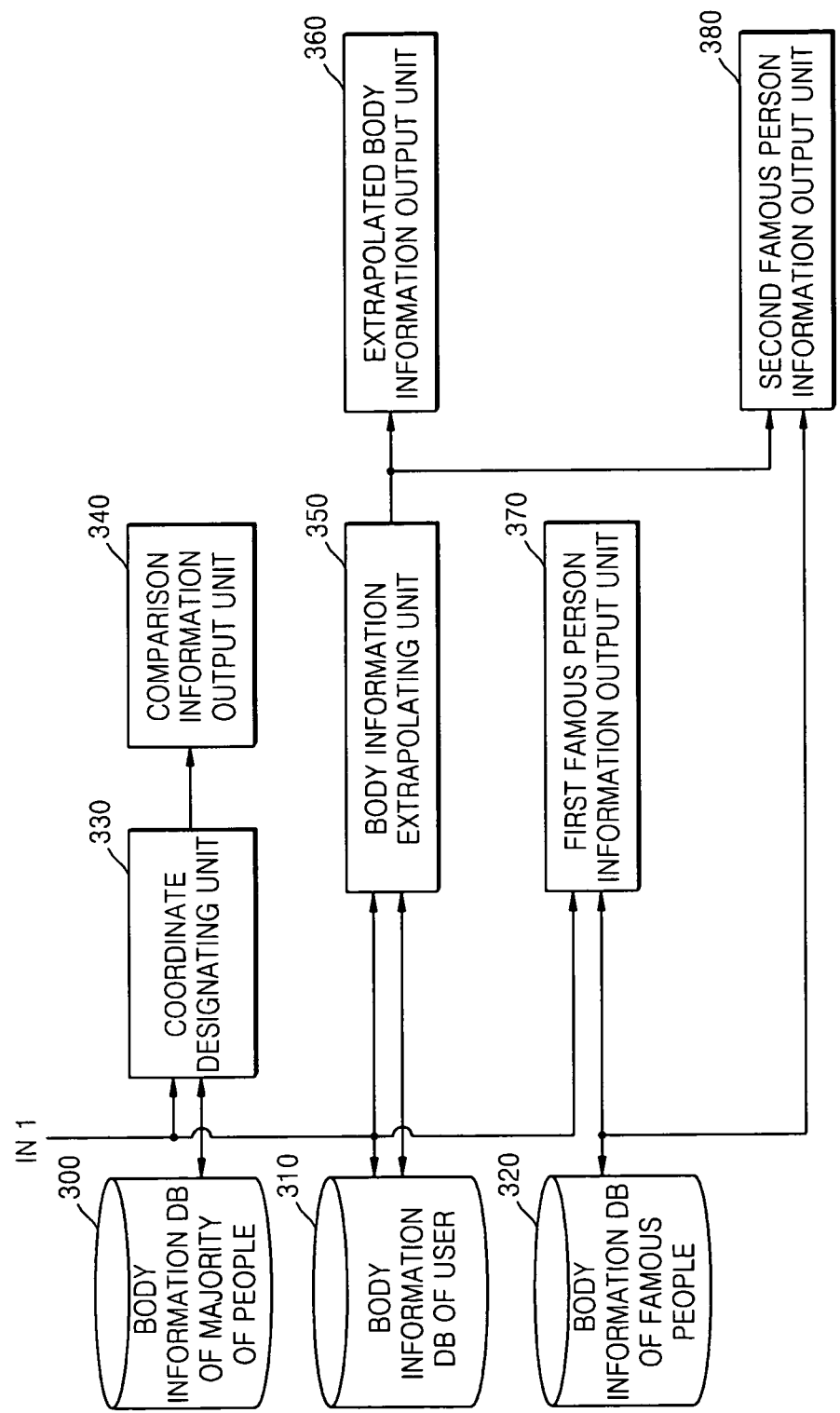

METHOD OF OUTPUTTING BODY INFORMATION AND APPARATUS THEREFOR

CROSS-REFERENCE TO RELATED APPLICATION

This application claims the benefit of Korean Patent Application No. 10-2005-0053057, filed on Jun. 20, 2005 in the Korean Intellectual Property Office, the disclosure of which is incorporated herein by reference.

BACKGROUND OF THE INVENTION

1. Field of the Invention

The present invention relates to a method of outputting body information, and more particularly, to a method and apparatus for outputting present and/or future body information of a user by comparing the body information of the user with average body information.

2. Description of Related Art

Conventionally, various methods of providing body information to users have been proposed. For example, the present state of the user's body is presented using text or graphs, or when the user inputs his or her body measurements, a three-dimensional image reflecting the body of the user is created. Furthermore, conventionally, to detect obesity or an abnormal state of the body, the body weight and body fat index are compared with the average weight and average body fat index, respectively.

However, since humans have diverse body figures according to exercise habits and hereditary factors, it is not reasonable to estimate an abnormal state using only weight and body fat index. There are people with small body weight with great body fat, and people with a great stomach circumference but average body weight and body fat index, and people with small body fat but great body weight. Thus, it can be difficult to determine an abnormal state based only on body weight and body fat index.

Furthermore, the user cannot recognize his or her body state simply from the text information or the graphs, and the user is not motivated to improve his or her body state with continuous interest.

BRIEF SUMMARY

An aspect of the present invention provides a method of and apparatus for outputting the body information of a user to compare the body information of the user with the average body information in three-dimensional coordinates.

According to an aspect of the present invention, there is provided a method of outputting the body information of a user, the method including: designating coordinates of the body information on a three dimensional graph having first, second, and third body information as coordinate axes; and outputting comparison information between the user's body figure and an average body figure based on the distance between the coordinates of the body information of the average body figure designated on a three-dimensional graph in advance and the coordinates of the body information of the user.

According to another aspect of the present invention, there is provided an apparatus for outputting the body information of a user, the apparatus including: a coordinate designating unit designating coordinates of the body information on a three dimensional graph having first, second, and third body information as coordinate axes; and a comparison information output unit outputting comparison information between the user's body figure and an average body figure based on the distance between the coordinates of the body information of the average body figure designated on a three-dimensional graph in advance and the coordinates of the body information of the user.

According to another aspect of the present invention, there is provided an apparatus for outputting body information of a user, the apparatus including: a designating means for designating coordinates of the body information on a three dimensional graph having first, second, and third body information as coordinate axes; and an outputting means for outputting comparison information between a body figure of the user and an average body figure based on distances between coordinates of the body information of the average body figure designated on the three-dimensional graph in advance and the coordinates of the body information of the user.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 2 is a table showing an example of the body information distribution;

FIG. 9 is a block diagram of an apparatus for outputting the body information of a user according to an embodiment of the present invention.

DETAILED DESCRIPTION OF EMBODIMENTS

Figure 1:
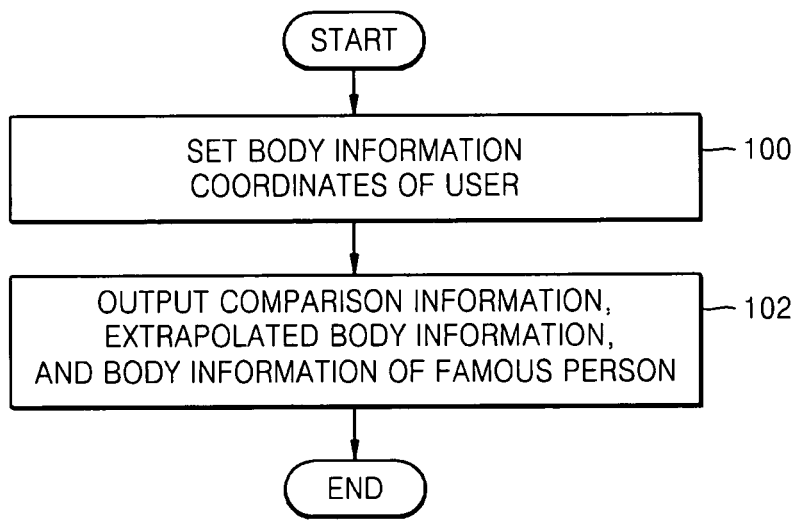
FIG. 1 is a flowchart illustrating a method of outputting body information of a user according to an embodiment of the present invention.

Reference will now be made in detail to embodiments of the present invention, examples of which are illustrated in the accompanying drawings, wherein like reference numerals refer to the like elements throughout. The embodiments are described below in order to explain the present invention by referring to the figures.

FIG. 1 is a flowchart illustrating a method of outputting body information of a user according to an embodiment of the present invention. First, body information coordinates based on first body information, second body information, and third body information are plotted on a three dimensional graph having the first body information, the second body information, and the third body information as coordinate axes (operation 100).

In the present embodiment, the first, second, and third body information respectively correspond to thigh circumference, stomach circumference, and body mass index (BMI). The BMI is a person's body weight divided by the square of the person's height. If the BMI is less than 20, the person is regarded to have low weight, if the BMI is between 20 and 24, the person is regarded to be of normal weight, and if the BMI is over 25, the person is regarded to be obese.

Being significant factors for determining a body figure, the stomach circumference, the thigh circumference, and the BMI are used as coordinates axes. However, these factors are merely exemplary, and other measurements such as chest circumference or hip circumference can also be used as coordinates axes.

FIG. 2 is a table showing an example of a body distribution. The body distribution includes thigh circumference and the average stomach circumference distributions according to age for Korean people.

Figure 3:
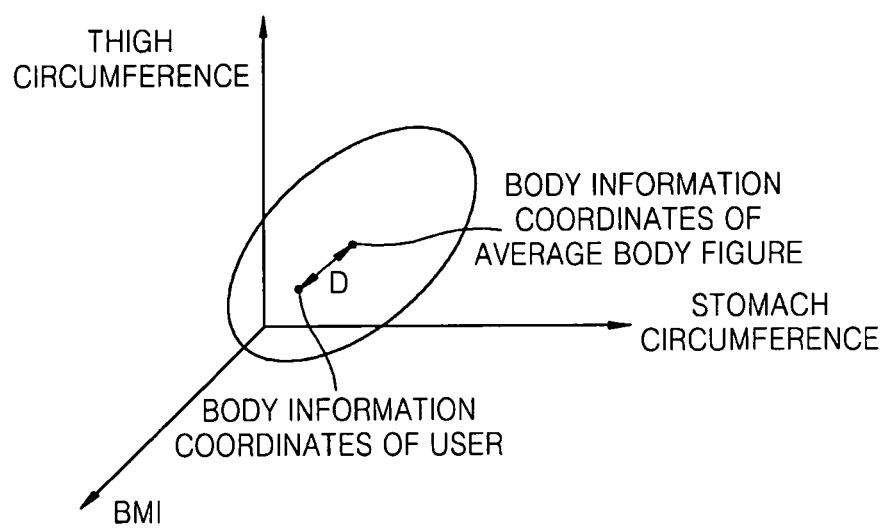
FIG. 3 is a three dimensional graph of body information including average body information.

FIG. 3 is a three dimensional graph of body information including average body information. When the stomach circumference, the thigh circumference, and the BMI of a large number of people are plotted on a three-dimensional graph, the distribution points forms an ellipsoid as illustrated in FIG. 3.

The center point of the ellipsoid formed by the distribution of the points is designated as the body information of an average body figure. The coordinates of the body information of an average body figure refers to, by way of non-limiting examples, the stomach circumference, the thigh circumference, and the BMI coordinates of the three dimensional graph which are obtained from the body information of an ideal body figure, and is independent of a sample group.

The information of the center point of the ellipsoid, that is, the coordinates of the body information of the average body figure, should be set before the coordinate point of the body information of the user are determined.

As illustrated in FIG. 3, the body information of the user is designated on a three dimensional graph using the body information of the user such as, by way of non-limiting examples, the stomach circumference, the thigh circumference, and the BMI.

Referring to FIG. 1, after operation 100, comparison information between the body figure of the user and the average body figure can be output as a distance D between the coordinate of the body information of the average body figure and the coordinate of the body information of the user (operation 102).

The comparison information, in particular, is output using principal component analysis (PCA).

Figure 4:
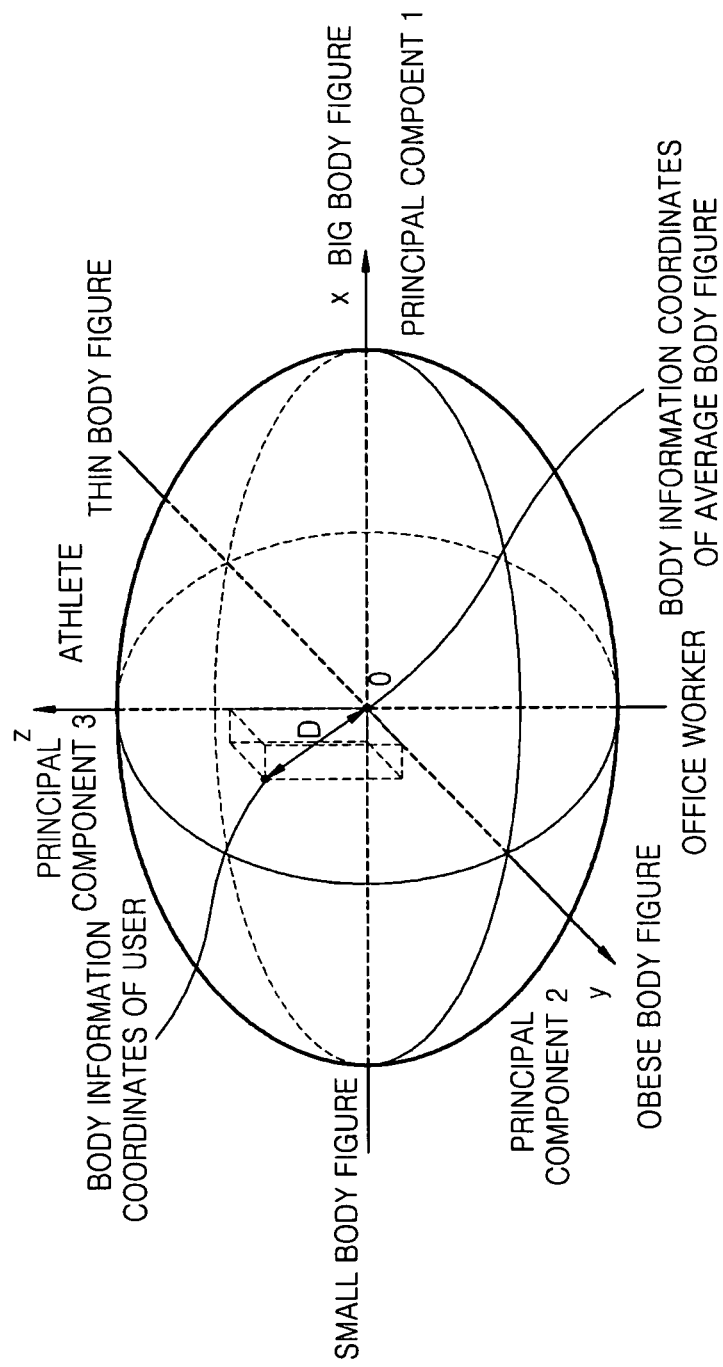
FIG. 4 illustrates body information with an ellipsoid of FIG. 3 and a method of using a principle component analysis (PCA) method with three-dimensional coordinates.

FIG. 4 illustrates the body information in the ellipsoid of FIG. 3 and a method of using the PCA method with three-dimensional coordinates. In the PCA, when variables that are related to each other are observed, a small number of new variables including the maximum information of the original variables are created.

As illustrated in FIG. 4, the x-axis represents the body information corresponding to a principal component 1 among various body information used as new coordinate axes. The y-axis represents the body information corresponding to a principal component 2 among various body information used as new coordinate axes. The z-axis represents the body information corresponding to a principal component 3 among various body information used as new coordinates.

The principal component 1 is the size of the body figure expressed. The size of the body figure increases as the value on the x-axis increases. For example, the stomach circumference and the thigh circumference can increase as the value on the x-axis increases. As the value on the x-axis decreases, the stomach circumference and the thigh circumference decrease and thus it is a small body figure. As illustrated in FIG. 4, the coordinate of the body information of the user has a negative x-value, and thus, the body figure of the user is smaller than the average body figure.

The principal component 2 indicates the degree of obesity. The degree of obesity increases as the value on the y-axis increases. For example, the body fat index can increase as the value on the y-axis increases, so it can be inferred that the body figure increases as the value on the y-axis increases. As illustrated in FIG. 4, since the coordinate of the body information of the user is located along the positive y-axis, it can be inferred that the user is a little more obese than the average body figure.

The principal component 3 indicates how similar the body information of the user is to the body information of an athlete. The greater the value on the z-axis, the more similar the body figure of the user is to the body figure of the athlete. The stomach circumference decreases and the thigh circumference increases as the value on the z-axis increases, and thus corresponds to the body figure of an athlete with muscles which result from exercise. The stomach circumference increases and the thigh circumference decreases as the value on the z-axis decreases, and thus corresponds to the body figure of an office worker with a large stomach circumference due to insufficient exercise. As illustrated in FIG. 4, since the coordinate of the body figure of the user is greater than 0, it can be inferred that the body figure of the user is more similar to the body figure of an athlete than the average body figure is to the body figure of an athlete. Comparison information indicates how much the body information of the user deviates from the body information of the average body figure is output.

Figure 5:
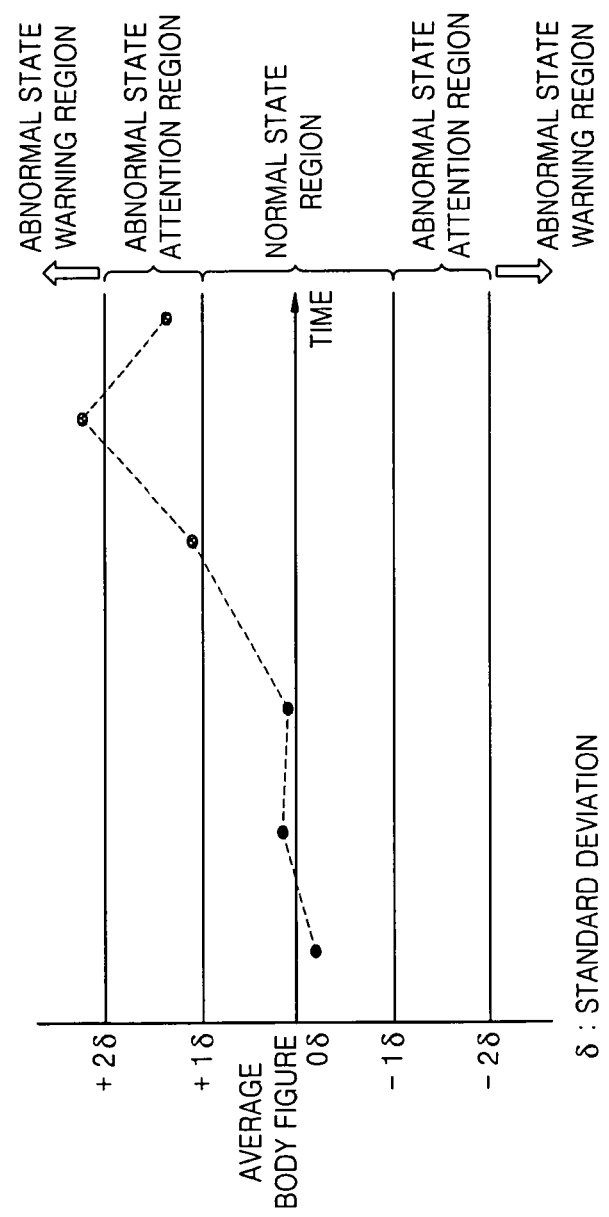
FIG. 5 illustrates an example of output comparison information.

FIG. 5 illustrates an example of an output of comparison information. As illustrated in FIG. 5, the degree of the deviation of the body figure of the user from the average body figure can be checked using the standard deviation. That is, if the body information of the user deviates to a great degree from the average body figure, a warning message is output so that the user can recognize that his or her body figure is not in a normal condition.

In operation 102 illustrated in FIG. 1, the body information of a famous person with body information similar to the present body information of the user can be output. A famous person is one who can be easily recognized through the media like entertainment celebrities or officials. For example, the human body image of a famous person may be output. As the body image of a famous person which is similar to the body information of the user is checked using a two-dimensional image or a three-dimensional image, the user can judge his or her body state more immediately and sensitively.

Figure 6:
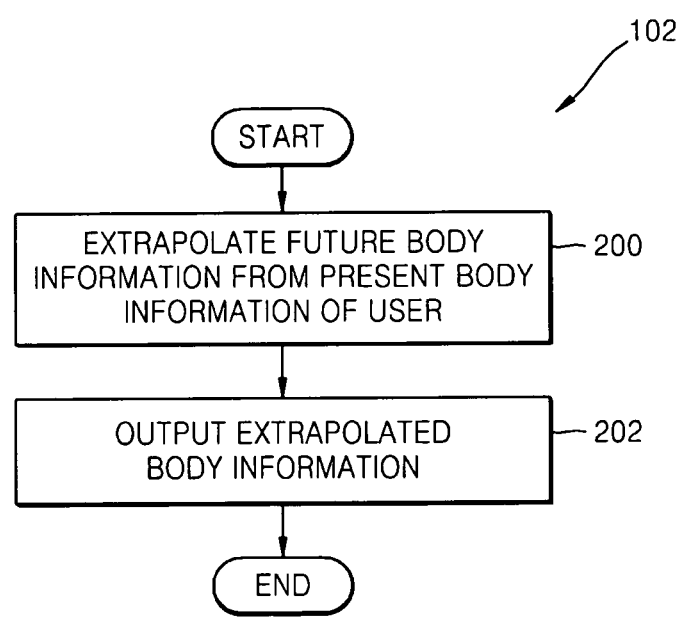
FIG. 6 is a flowchart of operation 102 illustrated in FIG. 1.

FIG. 6 is a flowchart of operation 102 illustrated in FIG. 1 in which future body information of the user is extrapolated from the present body information of the user. First, the future body information of the user is extrapolated from the user's present body information (operation 200). A database including the user's past and the present body information is used to extrapolate the user's future body information.

An autoregressive integrated moving average (ARIMA) statistics may be used to extrapolate the future body information in the present embodiment. ARIMA statistics refer to a time series prediction method including a combination of an autoregressive (AR) model and a moving average (MA) model. Equation 1 is the extrapolated algorithm when using the ARIMA (1,1,1) model.

$$Y_t = (1+\phi_1)Y_{t-1} - \phi_1 Y_{t-2} + \mu + e_t - \theta_1 e_{t-1},$$ [Equation 1]

where $Y_t$ refers to the future body information, for example the thigh circumference or the stomach circumference, $Y_{t-1}$ and $Y_{t-2}$ respectively refer to the present and past body information, $\phi$ and $\theta_1$ refer to weights, $\mu'$ refers to the compensation value of the average of the past and present body information, and $e_t$ and $e_{t-1}$ refer to the extrapolated error of each type of body information.

Figure 7:
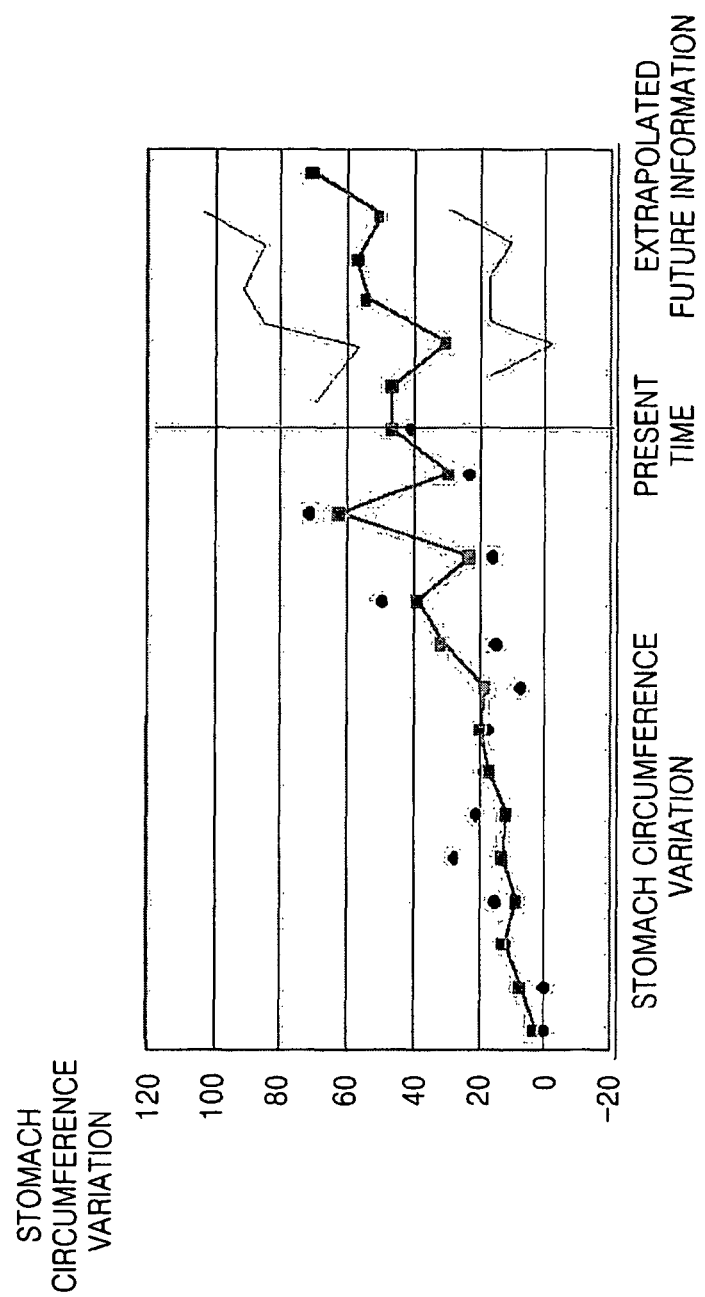
FIG. 7 illustrates further body information of a user extrapolated using the statistics of an autoregressive integrated moving average (ARIMA) model.

FIG. 7 illustrates the future body information of the user from extrapolated statistics of an ARIMA model. As illustrated in FIG. 7, the variation in the stomach circumference increases with time. Accordingly, when the user keeps the present dietary pattern, the user can check how the user's stomach circumference will change in the future.

If this state continues, the user will be obese in the future, and will recognize the necessity of improving his or her diet or doing exercise. Such a change in the body information according to diet or exercise can be presumed. That is, according to the ARIMA model, the diet and exercise indexes will be additionally reflected in the extrapolated future body information of the user. Equation 2 is an algorithm in which the diet and exercise indexes are reflected when using the ARIMA (p,d,q) model.

$$Y_t = \text{ARIMA}(p,d,q) + \alpha \times \text{dietary life index} + \beta \times \text{exercise index}, \quad \text{[Equation 2]}$$

where $\alpha$ and $\beta$ denote weights, the index of dietary life indicates the frequency of an irregular diet during a predetermined period, and the index of exercise indicates of the difference between the number of the days on which exercise was done and the number of the days on which exercise was not done divided by the length of a predetermined period.

Figure 8:
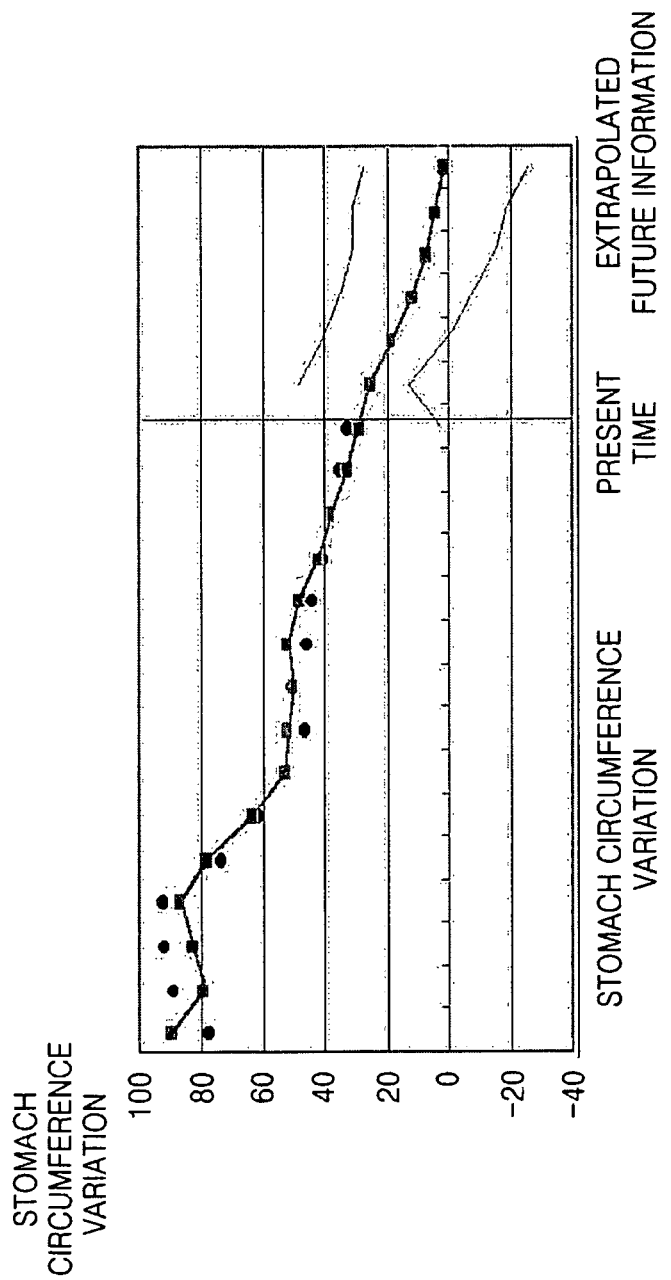
FIG. 8 illustrates further body information of a user using statistics of an ARIMA model reflecting dietary life index and exercise index.

FIG. 8 illustrates an example of future body information of the user using statistics of an ARIMA model reflecting eating habits and exercise. As illustrated in FIG. 8, it can be determined that the stomach circumference decreases with time according to the prescribed diet and exercise routine. After operation 200, the extrapolated future body information is output in operation 202.

In particular, the body image corresponding to the body information and the face of the user are constructed, and then the constructed images are output. For this, the face image of the user is provided in advance. The constructed images are two-dimensional or three-dimensional images. As the user can view his or her possible state, he or she can be motivated to bring a change to his or her body shape.

Meanwhile, the body information of a famous person which is similar to the extrapolated future body information can be output in operation 102. The body image of the famous person may be a two-dimensional or three-dimensional image. As the user can view his or her possible future state with the body image of a famous person, he or she can be motivated to bring a change to his or her body shape.

FIG. 9 is a block diagram of an apparatus for outputting the body information of the user according to an embodiment of the present invention. The apparatus includes a database of the body information of the majority of people 300, a database of the body information of the user 310, a database of body information of famous people 320, a coordinate designating unit 330, a comparison information output unit 340, a body information extrapolating unit 350, an extrapolated body information output unit 360, a first famous person information output unit 370, and a second famous person information output unit 380.

The body information of a plurality of people is stored in the database of body information of the majority of people 300. The body information of the majority of people may be the average body information of a sample group.

The past and present body information of the user is stored in the database of the body information of the user 310. The face image of the user is also stored in the database of the body information of the user 310.

The body information of famous people is stored in the database of the body information of famous people 320.

The coordinate designating unit 330 designates coordinates according to the first body information, the second body information, and the third body information of the user on a three-dimensional graph having the first body information, the second body information, and the third body information as coordinate axes, and outputs the designating result to the comparison information output unit 340.

The first body information, the second body information, and the third body information may, by way of non-limiting examples, respectively correspond to the thigh circumference, the stomach circumference, and the BMI.

The coordinate designating unit 330 receives the body information of the user through an input terminal IN1 and designates coordinates according to the body information of the user on a three-dimensional graph as illustrated in FIG. 3. The coordinate designating unit 330 also receives the body information of the people from the database of the body information of the majority of people 300 to designate coordinates of each person's body information on the three dimensional graph.

The center of an ellipsoid formed by the distribution of the coordinates of the body information of the majority of people is the coordinate of the body information of the average body figure.

The comparison information output unit 340 outputs the comparison information between the user and the average body figure based on the distance between the coordinates of the body information of the average body figure and the body information of the user, which are designated on the three-dimensional coordinates in advance.

The comparison information output unit 340 outputs the comparison information using PCA.

As illustrated in FIG. 4, the x-axis represents the body information corresponding to a principal component 1 among various body information used as new coordinate axes. The y-axis represents the body information corresponding to a principal component 2 among various body information used as new coordinate axes. The z-axis represents the body information corresponding to a principal component 3 among various body information used as new coordinates. The principal component 1 is the size of the body figure. The principal component 2 indicates the degree of obesity. Also, the principal component 3 indicates how similar the body information of the user is to the body information of an athlete.

The comparison information output unit 340 outputs a warning message according to how much the body information of the user deviates from the body information of the average body shape. As illustrated in FIG. 5, the deviation of the user body information from the standard body shape can be given in units on standard deviation of the body information.

The body information extrapolating unit 350 extrapolates the future body information of the user from the past and present body information of the user, and outputs the extrapolated result to the extrapolated information output unit 360 and the second famous person information output unit 380.

The body information extrapolating unit 350 extrapolates the future body information of the user referring to the present body information of the user received through the input terminal IN1 and the past body information of the user provided by the database of the body information of the user 310.

The ARIMA statistics are used to extrapolate the future body information in the body information extrapolating unit 350. Equation 1 is the extrapolated algorithm when using the ARIMA (1,1,1) model.

Also, the body information extrapolating unit 350 extrapolates the future body information of the user by reflecting the dietary life index and the exercise index in the ARIMA statistics. Equation 2 in which the dietary life index and the exercise index are reflected is the extrapolation algorithm when using the ARIMA (p,d,q) model.

The extrapolated information output unit 360 outputs the body information extrapolated by the body information extrapolating unit 350.

The extrapolated information output unit 360 compounds the extrapolated body information image with the face image of the user, and then outputs the compounded human body image. For this, the extrapolated information output unit 360 receives the face image information of the user from the database of the body information of the user 310.

The extrapolated information output unit 360 outputs a two-dimensional or three-dimensional constructed human body image.

The first famous person information output unit 370 outputs the body information of a famous person whose body information is similar to the present body information of the user. The first famous person information output unit 370 requests from the database of the body information of a famous person 320 body information of a famous person whose body information is similar to the present body information of the user received from the input terminal IN1, and outputs the requested famous person body information.

The first famous person information output unit 370 outputs the human body image of the famous person whose body information is similar to the present body information as of the user as a two-dimensional image or a three-dimensional image.

The second famous person information output unit 380 outputs the body information of a famous person whose body information is similar to the extrapolated body information. The second famous person information output unit 380 requests from the database of the body information of a famous person 320 body information of a famous person whose body information is similar to the extrapolated body information of the user extrapolated by the body information extrapolating unit 350 and outputs the requested famous person body information.

The second famous person information output unit 380 outputs the human body image of the famous person whose body information is similar to the extrapolated information of the user as a two-dimensional graphic image or a three-dimensional image.

Embodiments of the present invention can also be embodied as computer readable code on a computer readable recording medium. The computer readable recording medium is any data storage device that can store data which can be thereafter read by a computer system. Examples of the computer readable recording medium include magnetic storing media (such as read-only memory (ROM), floppy disks, hard disks, and magnetic tapes), optical reading devices (such as CD-ROMs, DVD), and carrier waves (such as data transmission through the Internet). The computer readable recording medium can also be distributed over network coupled computer systems so that the computer readable code is stored and executed in a distributed fashion.

In the method and apparatus for providing the body information of the user according to the above-described embodiments of the present invention, the body information of the average body figure and the body information of the user are compared synthetically to help the user recognize his or her present body state more objectively and accurately.

Furthermore, in the method and apparatus for providing the body information of the user according to the above-described embodiments of the present invention, the future body information is extrapolated and analysed using the accumulated body information of the user to help the user determine his or her likely weight increase or decrease and inform the user of an impending abnormal state. The future body information can be predicted using only the past body information, which is called prescription extrapolation, or using information such as diet and exercise habits synthetically.

Moreover, in the method and apparatus for providing the body information of the user according to the above-described embodiments of the present invention, the future body information of the user is expressed using a human body model to help the user recognize his or her future body change sensitively and immediately.

Since the image of a famous person whose body information is similar to the present or future body information of the user is used for comparison in the methods and apparatus for providing the body information of the user in the above-described embodiments of the present invention, the user can be motivated to change his or her body figure to the average body figure.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A method of outputting body information of a user, comprising:
designating, using a sufficiently programmed computer, a coordinate of first, second, and third body information of the user on a three-dimensional graph having first, second, and third body information as coordinate axes; and
outputting comparison information, including combined body information of the first, second, and third body information, between a body figure of the user and an average body figure based on a distance between a coordinate of the first, second, and third body information of the average body figure designated on the three-dimensional graph obtained in advance, and the coordinate of the first, second, and third body information of the user.

2. The method of claim 1, wherein, coordinates of the first, second, and third body information of a large number of people are designated on the three-dimensional graph, and
the coordinate of the first, second, and third body information of the average body figure are determined by a center coordinate of an ellipsoid formed by a distribution of the designated coordinates of the first, second, and third body information corresponding to the large number of people.

3. The method of claim 1, wherein the comparison information is obtained using a principal component analysis (PCA).

4. The method of claim 1, wherein the outputting comparison information comprises outputting a warning message according to a deviation of the body information of the user from body information of the average body figure.

5. The method of claim 1, wherein the first, second, third body information are respectively thigh circumference, stomach circumference, and body mass index (BMI).

6. The method of claim 1, further comprising:
extrapolating future body information from present body information; and
outputting the extrapolated future body information.

7. The method of claim 6, wherein the extrapolating comprises using autoregressive integrated moving average (ARIMA) statistics to extrapolate the future body information.

8. The method of claim 7, wherein the extrapolating comprises using an ARIMA statistics reflecting a dietary index and an exercise index to extrapolate the future body information.

9. The method of claim 6, wherein the outputting the extrapolated future body information comprises constructing an image indicated by the extrapolated future body information using a face image of the user and outputting the constructed image.

10. The method of claim 9, wherein the outputting the extrapolated future body information comprises outputting a two-dimensional image or a three-dimensional image as the constructed image.

11. The method of claim 1, further comprising outputting body information of a famous person whose body information is similar to present body information of the user.

12. The method of claim 11, further comprising outputting a human body image of the famous person whose body information is similar to the present body information of the user.

13. The method of claim 6, further comprising outputting body information of a famous person whose body information is similar to the extrapolated future body information.

14. The method of claim 13, further comprising outputting a human body image of the famous person whose body information is similar to the extrapolated future body information of the user.

15. A non-transitory computer readable medium having embodied thereon a computer program performing for the method according to claim 1.

16. An apparatus for outputting body information of a user, comprising:
a processor;
a display to display body information to the user;
a storage device to store body information of the user and body information of at least one other person;
a coordinate designating unit to designate a coordinate of first, second, and third body information of the user on a three-dimensional graph having first, second, and third body information as coordinate axes; and
a comparison information output unit to output to the display comparison information, including combined body information of the first, second, and third body information, between a body figure of the user and an average body figure based on a distance between a coordinate of the first, second, and third body information of the average body figure designated on the three-dimensional graph stored in advance in the storage device, and the coordinate of the first, second, and third body information of the user,
wherein the coordinate designating unit uses the processor to designate the coordinate of the first, second, and third body information and the comparison information output unit uses the processor to output comparison information to the display.

17. The apparatus of claim 16, wherein, coordinates of the first, second, and third body information of a large number of people are designated on the three-dimensional graph, and
the coordinate of the first, second, and third body information of the average body figure are determined by a center coordinate of an ellipsoid formed by a distribution of the designated coordinate of the first, second, and third body information corresponding to the large number of people.

18. The apparatus of claim 16, wherein the comparison information output unit uses principal component analysis (PCA) to output the comparison information.

19. The apparatus of claim 16, wherein the comparison information output unit outputs a warning message according to a deviation of the body information of the user from the body information of the average body figure.

20. The apparatus of claim 16, wherein the first, second, third body information are respectively thigh circumference, stomach circumference, and body mass index (BMI).

21. The apparatus of claim 16, further comprising:
a body information extrapolating unit to extrapolate future body information from present body information; and
an extrapolated information output unit to output the extrapolated body information.

22. The apparatus of claim 21, wherein the body information extrapolating unit uses autoregressive integrated moving average (ARIMA) statistics to extrapolate the future body information.

23. The apparatus of claim 22, wherein the body information extrapolating unit uses ARIMA statistics reflecting a dietary index and an exercise index to extrapolate the future body information.

24. The apparatus of claim 21, wherein the extrapolated information output unit constructs an image indicated by the extrapolated body information using a face image of the user and outputs the constructed image.

25. The apparatus of claim 24, wherein the extrapolated body information output unit outputs a two-dimensional image or a three-dimensional image as the constructed image.

26. The apparatus of claim 16, further comprising a first famous person information output unit to output body information of a famous person whose body information is similar to present body information of the user.

27. The apparatus of claim 26, wherein the first famous person information output unit outputs a human body image of the famous person whose body information is similar to the present body information of the user.

28. The apparatus of claim 21, further comprising a second famous person information output unit to output body information of a famous person whose body information is similar to the extrapolated body information of the user.

29. The apparatus of claim 28, wherein the second famous person information output unit outputs a human body image of the famous person whose body information is similar to the extrapolated future body information of the user.

30. The apparatus of claim 16, further comprising a database of the body information of the user.

31. The apparatus of claim 16, further comprising a database of body information of a sample of a population.

32. The apparatus of claim 26, further comprising a database of the body information of the famous person.

33. An apparatus for outputting body information of a user, comprising:
a processor;
a display means for displaying body information to the user;

a storage means for storing body information of the user and body information of at least one other person;

a designating means for designating a coordinate of first, second, and third the body information of the user on a three-dimensional graph having first, second, and third body information as coordinate axes; and an outputting means for outputting to the display comparison information, including combined body information of the first, second, and third body information, between a body figure of the user and an average body figure based on a distance between a coordinate of the first, second, and third body information of the average body figure designated on the three-dimensional graph stored in advance in the storage means, and the coordinate of the first, second, and third body information of the user, wherein the designating means uses the processor for designating the coordinate of the first, second, and third body information and the output means uses the processor for outputting comparison information to the display means.

* * * * *

UNITED STATES PATENT AND TRADEMARK OFFICE
CERTIFICATE OF CORRECTION

PATENT NO.        : 8,423,295 B2
APPLICATION NO.   : 11/445152
DATED             : April 16, 2013
INVENTOR(S)       : Woo-young Jang et al.

It is certified that error appears in the above-identified patent and that said Letters Patent is hereby corrected as shown below:

In the Claims:

Column 11, Line 4, In Claim 33, delete "the body" and insert -- body --, therefor.

Signed and Sealed this
Sixth Day of August, 2013

Teresa Stanek Rea
*Acting Director of the United States Patent and Trademark Office*